(12) United States Patent
Chung et al.

(10) Patent No.: US 6,719,763 B2
(45) Date of Patent: Apr. 13, 2004

(54) ENDOSCOPIC SUTURING DEVICE

(75) Inventors: Sydney Sheung Chee Chung, New Territories (CN); Hitoshi Mizuno, Koganei (JP); Tetsuya Yamamoto, Hidaka (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/964,815

(22) Filed: Sep. 28, 2001

(65) Prior Publication Data

US 2002/0116011 A1 Aug. 22, 2002

Related U.S. Application Data (60) Provisional application No. 60/236,365, filed on Sep. 29, 2000.

(51) Int. Cl.⁷ .............................................. A61B 17/04
(52) U.S. Cl. ........................ 606/144; 606/139; 600/104
(58) Field of Search ........................ 606/139, 144–148, 606/205, 222, 224; 600/104, 121, 123, 153

(56) References Cited

U.S. PATENT DOCUMENTS

| | | | | |
|---|---|---|---|---|
| 3,168,097 A | | 2/1965 | Dormia | |
| 5,037,433 A | * | 8/1991 | Wilk et al. | 606/139 |
| 5,364,408 A | * | 11/1994 | Gordon | 606/144 |
| 5,374,275 A | | 12/1994 | Bradley et al. | |
| 5,437,680 A | * | 8/1995 | Yoon | 606/139 |
| 5,470,338 A | * | 11/1995 | Whitfield et al. | 606/144 |
| 5,665,096 A | * | 9/1997 | Yoon | 606/139 |
| 5,766,186 A | * | 6/1998 | Faraz et al. | 606/145 |
| 2002/0116010 A1 | | 8/2002 | Chung et al. | |

* cited by examiner

Primary Examiner—Julian W. Woo
(74) Attorney, Agent, or Firm—Frishauf, Holtz, Goodman & Chick, P.C.

(57) ABSTRACT

An endoscopic suturing device includes an endoscope, a curved needle detachably arranged at the distal end portion of or integrally embedded in the endoscope for suturing a tissue of the living body, a suture for suturing said tissue with the curved needle, and a drive arranged on the endoscope and operating the curved needle.

14 Claims, 9 Drawing Sheets

ENDOSCOPIC SUTURING DEVICE

CROSS REFERENCE TO RELATED APPLICATIONS

This application claims priority to provisional application Ser. No. 60/236,365 filed Sep. 29, 2000.

FIELD OF THE INVENTION

The present invention relates to a suturing device used with an endoscope for suturing a tissue in a body cavity or stanching blood.

BACKGROUND OF THE INVENTION

Endoscopic suturing devices are known. One such device is described, for example, in U.S. Pat. No. 5,037,433 to Peter J. Wilk.

Recently, developments in the endoscopic treatment procedure have been remarkable: medical treatment may be received without major surgery in some cases such as an abdominal section. Since, suturing of tissue after perforation in a body cavity or stanching of blood are very important endoscopic techniques, efforts have been made to develop such techniques.

For example, U.S. Pat. No. 5,037,433 discloses a method in which an elongate flexible outer tubular endoscope member comprises multiple flexible lumens, a flexible endoscope being arranged in one of said lumens, an inner tubular member being arranged in another one of the lumens, and a forceps device with forceps in an elongate flexible body portion being arranged in a further one of the lumens. A curved needle can be elastically transformed and inserted into the inner tube in a stretched-straight state. Also the curved needle has a suture member on the proximal end side. For suturing, the curved needle is pushed out from the inner tube by pushing the rod members, which are arranged to push out the curved needle, arranged on the distal end of the inner tube. At the same time, the restoring force is utilized to suture a wound in a body cavity.

Since the device disclosed in U.S. Pat. No. 5,037,433 uses an elastic curved needle inserted in a narrow inner tube in a stretched straight state. However, the curved needle cannot stick deeply into the tissue because the sticking force is reduced by resistance between the inner tube and the curved needle caused by the restoring power of elasticity of the curved needle when the curved needle is pushed out from the inner tube by the rod member.

In addition, the flexible outer tubular endoscope member cannot be bent sufficiently because the rod member has a certain rigidity to push out the curved needle from the inner tube. Further, since the curved needle cannot be backed into the inner tube once the curved needle is stuck into the tissue, adjustment cannot be made when the curved needle slips off the target. Moreover, a greater diameter of the flexible outer tubular endoscope member due to its multi-lumen structure including an endoscope, suturing member, and forceps device may increase the pain of the patient. Furthermore, the separation structure of the endoscope and suturing device may decrease the manipulability.

SUMMARY OF THE INVENTION

By solving the above-mentioned problems, the present invention is intended to provide an endoscopic suturing device in which the sticking force can be efficiently transmitted to the curved needle at any angle of the endoscope, the sticking location can be corrected several times, the outer diameter of the entire body can be smaller, the manipulability of endoscope and suturing device can be improved, and the target location can be easily approached with the operating angle of the endoscope.

This is done with an endoscopic suturing device comprising an endoscope, a curved needle detachably arranged at the distal end portion of or integrally embedded in the endoscope for suturing a tissue of the living body, a suture for suturing the tissue with the curved needle, and a driving means arranged on the endoscope and operating the curved needle.

The suturing device, detachably or integrally attached to the end of the endoscope, has a curved needle detachably or integrally attached to the driving member. The curved needle has a perforation through which a suture can pass: the suture passing through a channel of the endoscope from the proximal end to the distal end passes through the perforation.

The endoscope, at the distal end of which the suturing device with the curved needle contained in the protective member is mounted, is introduced to a suturing target in a human being or animal body cavity. The curved needle is moved to the target region by manipulating the control section arranged on the proximal side of the endoscope for controlling the curved needle, and the suturing device is pressed on the region to be sutured, for example, by angling the endoscope. While the suturing device is being pressed on the region, the curved needle is stuck into the tissue by manipulating its control section.

After sticking into the tissue, the tip of the needle and the suture are confirmed on the surface of the tissue in the field of view of the endoscope, an end of the suture is grasped with the grasping member and brought to the proximal side with the grasping member. The curved needle is returned with the suture grasped on the proximal side of the endoscope, and the curved needle is stuck into another region near the already stuck location. Then, another end of the suture is grasped with the grasping member and brought to the proximal side with the grasping member.

A knot is made with the two obtained ends, and pushed forward to the target region through a channel of the endoscope by the knot pressure. By repeating the above-mentioned process several times, the tissue can be sutured.

DETAILED DESCRIPTION

Figure 1:
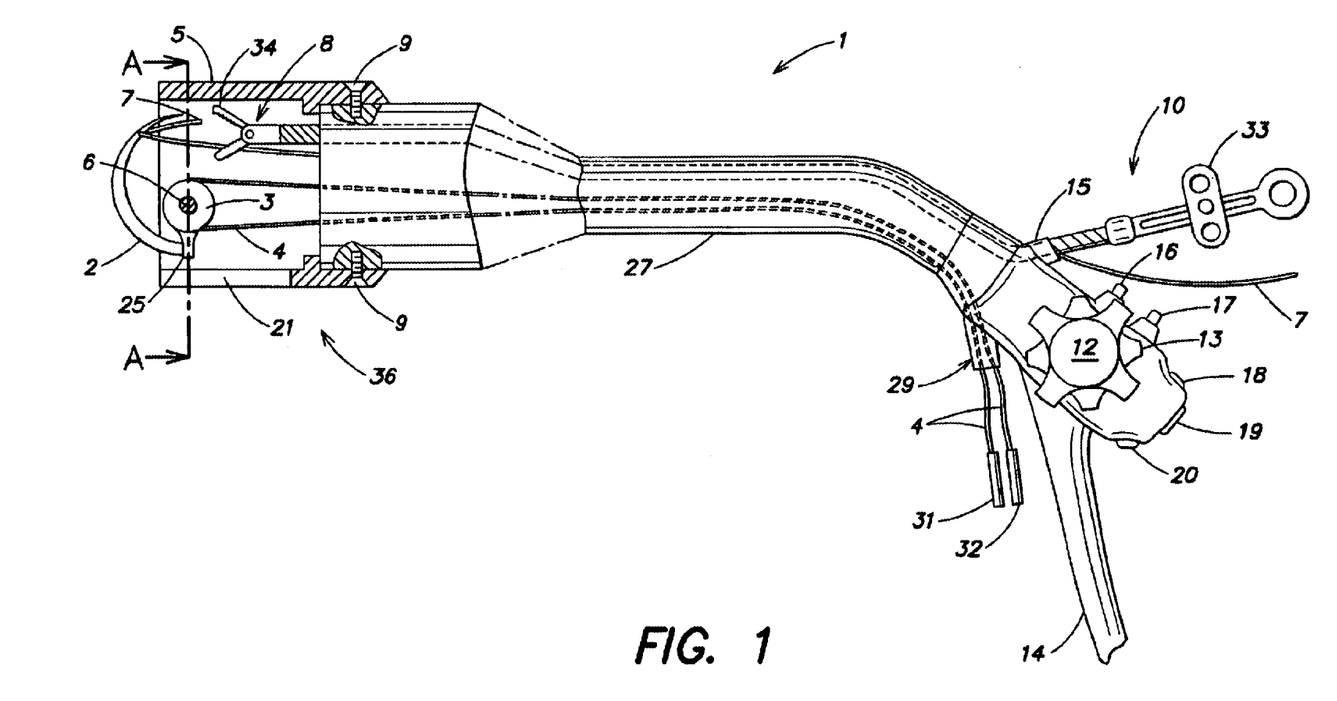
FIG. 1 is a view showing the general construction of an endoscopic suturing device attached to the distal end of an endoscope according to the present invention.
Figure 2:
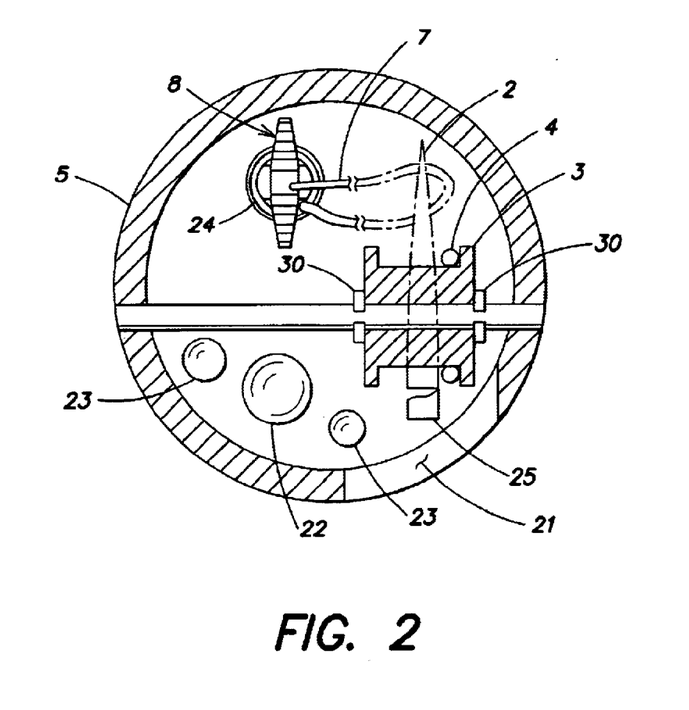
FIG. 2 is a sectional view taken along the line A—A of FIG. 1.

A first embodiment of the present invention is shown in FIGS. 1 through 13. As shown in FIGS. 1 and 2, the endoscope 27 has a CCD camera 22, light-guide 23, and forceps channel 24 in its distal end portion, while an up-down handle 12 and a right-left handle 13 for controlling the tip bending section of the endoscope 27, a suction button 17, an air/water-supply button 16, an image pickup button 18, a shutter button 20, an image enlarging button 19, an air/water-supply tube, light guide, suction tube, a channel opening 15, a universal cord 14 containing various cords for photographing and a curved needle driving mechanism fixation section 29 on its proximal side. In the present embodiment, a videoscope with a CCD is used, but a fiberscope with eyepieces may be used.

At the distal end of the endoscope 27, a protective member 5 is detachably or integrally attached with a bolt 9 so that the curved needle 2 does not injure the human body when the device 1 is inserted into a body cavity, and a slit 21 is arranged so that the curved needle 2 can rotate. An axle 6 is fixed on the protective member 5 that is almost orthogonal to the longitudinal axis of the endoscope 27. A rotation disk 3 is rotatably arranged around the axle 6, and a stop member 30 like a C-ring is arranged so that the rotation disc cannot move on the axle 6 in the axial direction. The curved needle 2 is detachably or integrally attached to the rotation disk 3 via an arm 25, and, as shown FIGS. 1 and 2, the operating wire 4 for rotating the rotation disk is interlinked at least with part of the rotation disk 3 by brazing, soldering, or friction so that the power of the operating wire 4 can be positively transmitted without slippage. On the proximal side, the two ends of the operating wire 4 are separately fixed to curved needle control sections 31 and 32: the curved needle 2 can be manipulated by alternately pushing and pulling the control sections 31 and 32. It is needless to say that the curved needle can be rotated forward and backward by manipulating the control sections 31 and 32.

Figure 3:
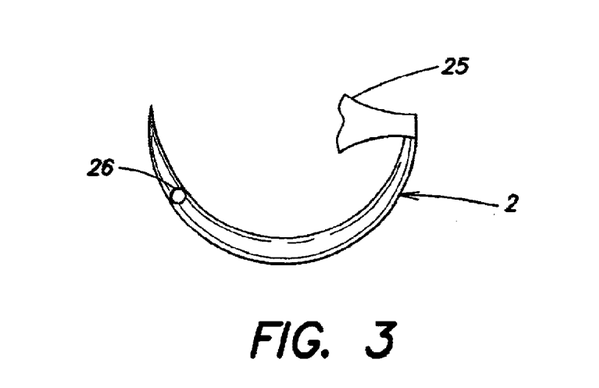
FIG. 3 is a detailed view of a curved needle.
Figure 4:
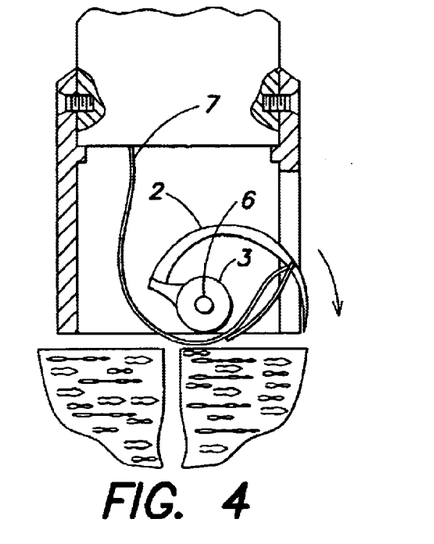
FIGS. 4 through 13 show the suturing process of the first embodiment 1.

On the other hand, as shown in FIG. 3, a small hole 26 through which a suture 7 can pass is arranged on the sharp-edged end side of the curved needle 2, and, as shown FIGS. 1 and 2, the suture 7 passes through the hole 26. As shown in FIG. 1, the proximal end portion of the suture 7 is removed from the body cavity through the channel opening 15 via the forceps channel 24.

A suture grasping/withdrawing means 8 is detachably arranged inside the endoscopic suturing device 1 to grasp one end of the suture 7, and withdraw it from the body, after the curved needle 2 is stuck into a tissue. Although the grasping forceps is used in the present embodiment, any appropriate tool may be used for the above-mentioned grasping and withdrawing operation. The suture grasping/withdrawing means 8 are situated at an appropriate location so as to grasp one end of the suture 7 in an easy manner. The suture 7 passes through the forceps channel 24 like the suture grasping/withdrawing means 8. A slider 33 is attached to the suture grasping control section 10: the grasping member 34 arranged on the distal end can be opened or closed to grasp the suture 7 by pushing or pulling the slider 33.

With reference to FIGS. 1 through 3, the manner of assembling the first embodiment 1 will be described. While the suturing unit 36 comprising a curved needle 2, rotation disk 3, operating wire 4, protective member 5, and axle 6 remains detached from the endoscope, the suture 7 is passed through the hole 26. The suture grasping/withdrawing means 8 is inserted into the channel opening 15, and, as shown FIG. 1, one end of the suture 7, grasped by the suture grasping/withdrawing means 8, is taken out from the channel opening 15.

Next, the two ends of the operating wire 4 are grasped by the suture grasping/withdrawing means 8 inserted from the curved needle driving mechanism fixation section 29, and brought on the proximal side of the endoscope 27. Next, the suturing unit 36 is fixed to the distal end of the endoscope 27 with a bolt 9.

Next, the suture grasping/withdrawing means 8 is inserted into the forceps channel 24, like the suture 7, until it is in such a position as it can grasp the suture 7 after the needle is stuck into a tissue. The suture grasping/withdrawing means 8 may be inserted when the suture 7 is grasped and withdrawn after sticking.

Next, the suturing process will be described with reference to FIGS. 4 through 13.

(1.) The distal end of the endoscopic suturing device 1 is inserted into the body cavity for the region to be sutured.

(2.) The curved needle 2 is brought to the location shown in FIG. 4 by backwardly rotating the rotation disk 3 by pulling on the curved needle control section 31.

Figure 5:
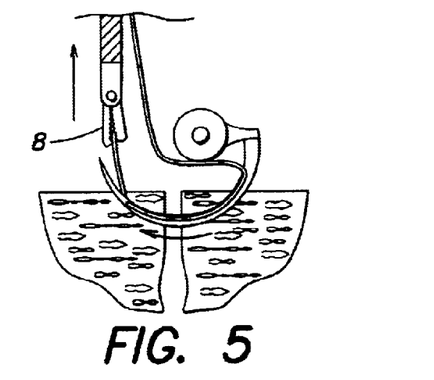
Figure 6:
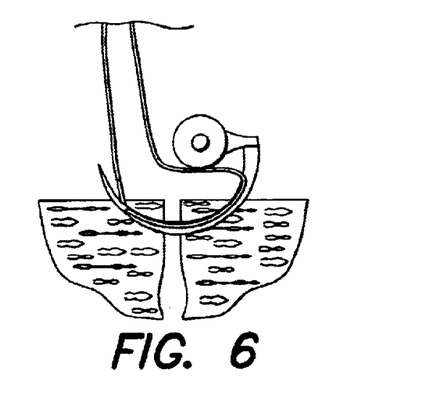

(3.) After the curved needle 2 is stuck into the region to be sutured in an almost transverse way, as shown in FIG. 5, by forwardly rotating the rotation disk 3 by pulling the curved needle control section 32, one end of the suture 7 that is out of the tissue is grasped by the suture grasping/withdrawing means 8 inserted from the forceps channel 24, and brought out from the body cavity as shown in FIG. 6.

Figure 7:
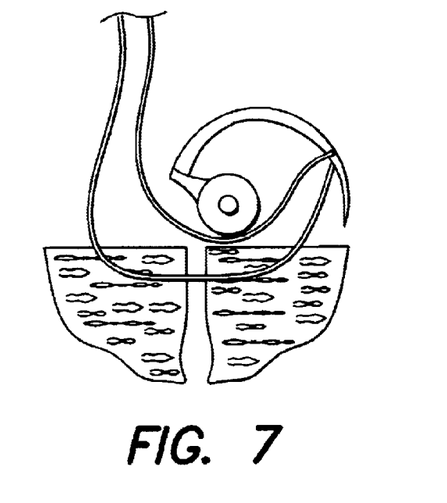

(4.) As shown in FIG. 7, the curved needle 2 is rotated in the backward direction, and then removed from the tissue once.

Figure 8:
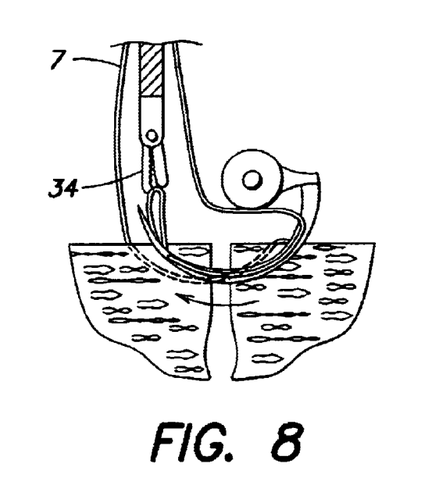
Figure 9:
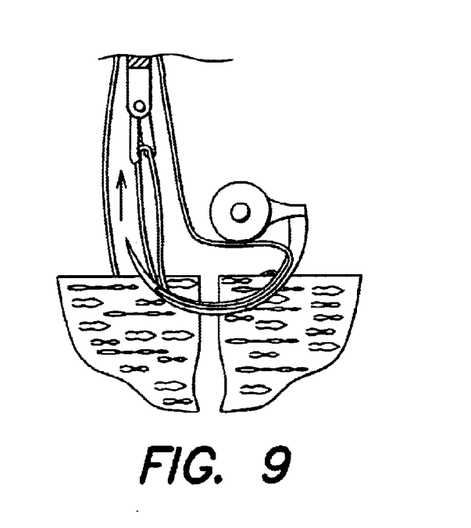
Figure 10:
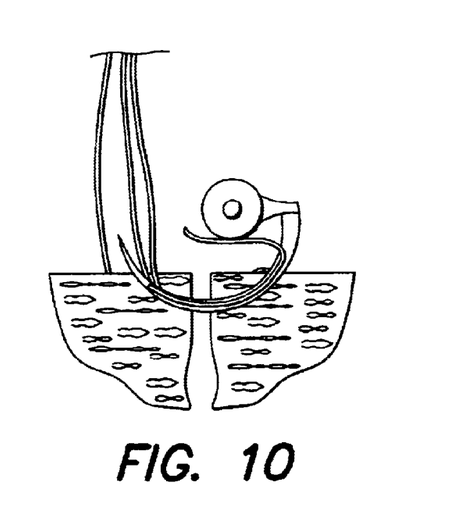
Figure 11:
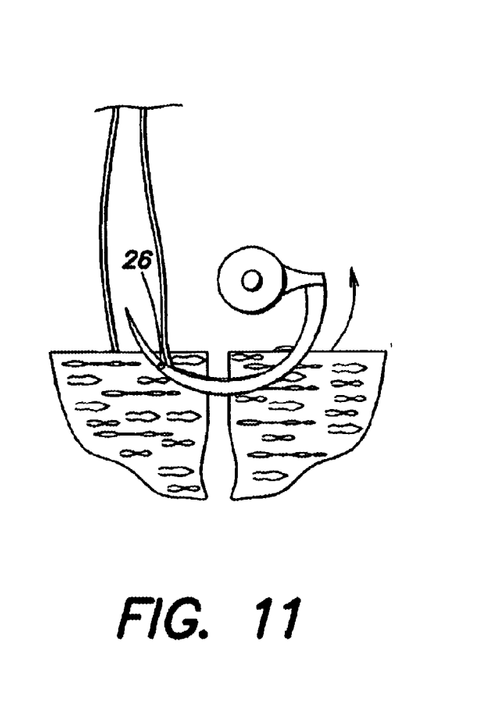

(5.) As shown in FIG. 8, the needle is stuck onto some location a little bit away from the above-mentioned sutured point by angling the scope, and, as shown in FIGS. 9 through 11, another end of the suture 7 is brought out from the body cavity without pulling the portion used for suturing.

Figure 12:
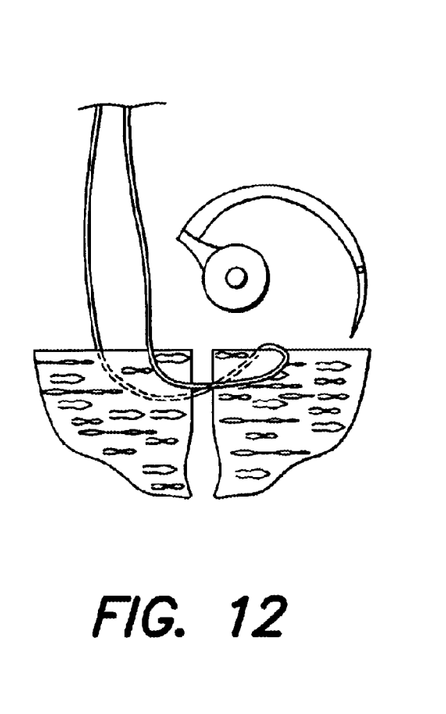

(6.) As shown in FIG. 12, the curved needle 2 is pulled from the tissue once again.

Figure 13:
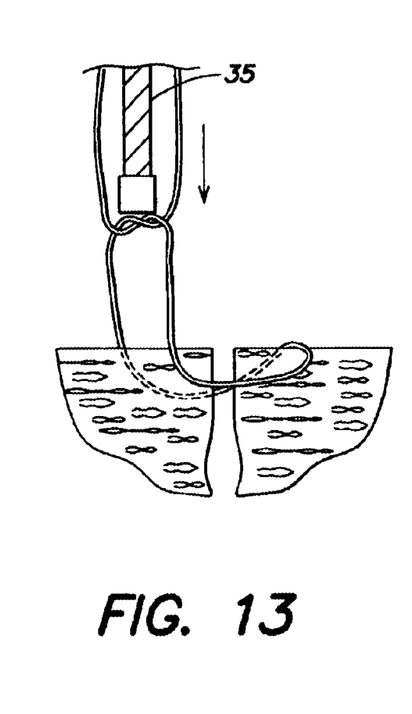

(7.) As shown in FIG. 13, the two end portions of the suture 7 brought out from the body cavity are knotted, and the knot is pushed to the sutured region through the forceps channel 24 by the knot pusher 35. The suturing process is completed after repeating this procedure several times so as not to loosen the knot.

This embodiment has a number of merits. Since the sticking force can be efficiently transmitted to the curved needle for any bending state of the endoscope, the needle can be deeply stuck into the tissue. In addition, the suturing device can be inserted into a narrow body cavity because the general outer diameter can be reduced, and the manipulability of the endoscope is improved and suturing procedure is easier because the suturing device is integrally arranged on the endoscope.

A second embodiment is shown in FIGS. 14 through 18. Since the proximal side of the endoscopic suturing device 1 of this embodiment has the same construction as that of the first embodiment, a description is omitted. As in the first embodiment, a CCD camera 22, light guide 23, and forceps channel 24 are arranged in the distal end of the endoscope 27.

Figure 14:
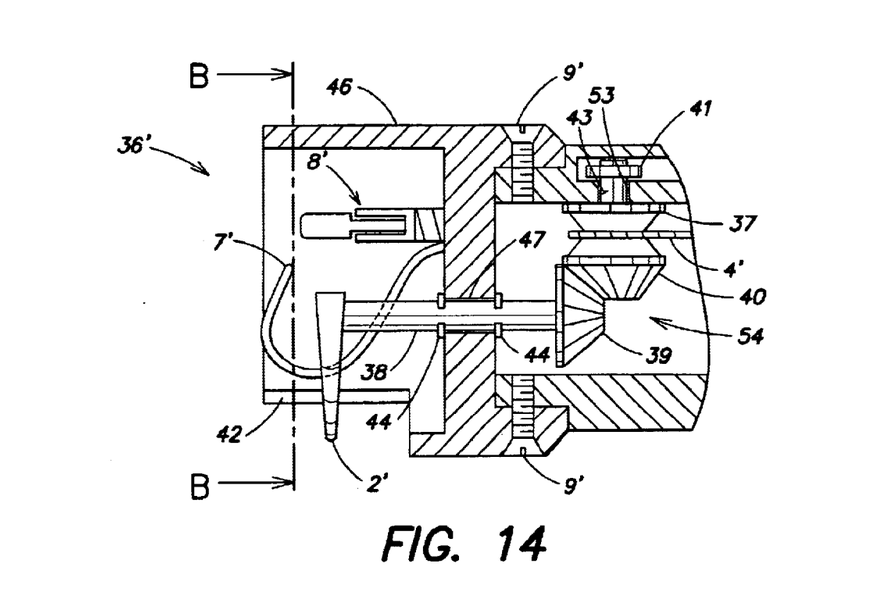
FIG. 14 is a view for the endoscopic suturing device 1 whose distal end portion is modified.

As shown in FIGS. 1 and 14, a protective member 46 is detachably or integrally attached to the distal end of the endoscope 27 with a bolt 9 so that the curved needle 2 cannot injure the human body when the endoscopic suturing device 1 is inserted into a body cavity, and a slit 42 is arranged so that the curved needle 2 can be rotated. The protective member is almost circular, and has a diameter almost equal to the outer diameter of said endoscope.

Figure 17:
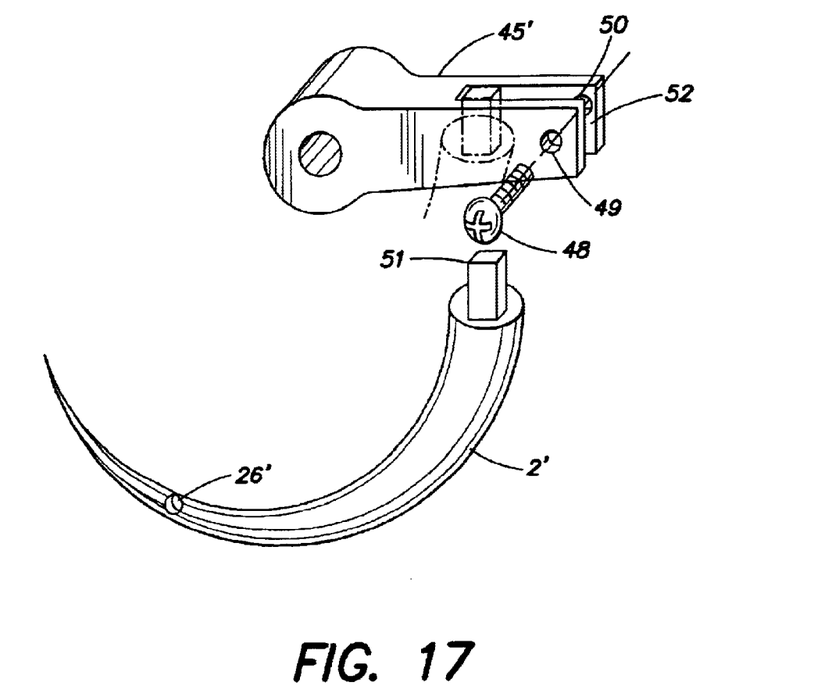
FIG. 17 illustrates a possible configuration of the curved needle.
Figure 18:
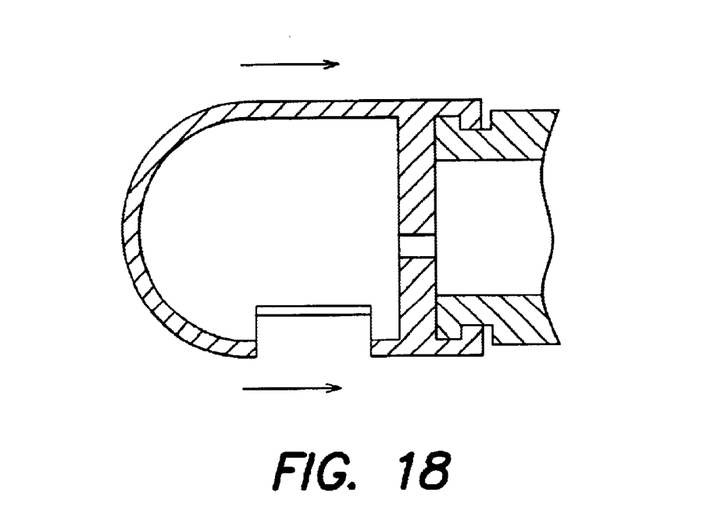
FIG. 18 illustrates a construction utilizing elastic deformation and claws.

If the protective member 46 is detachably attached to the distal end of the endoscope 27, any attachment means may be used. For example, as shown in FIG. 18, a construction utilizing elastic deformation and claws may be employed. An axle 38 almost in parallel with the longitudinal axis of the endoscope 27 is rotatably arranged in the protective member 46. On the axle 38, the curved needle 2 is fixed at an appropriate location via an arm section 45 by brazing or some other means, while a bevel gear 39 is also fixed on the proximal side by brazing or some other means. The axle section 38 between the curved needle 2 and bevel gear 39 is fit into the hole 47 arranged on the protective member 46, and a stop member 44 like a C-ring is arranged on the both sides of the hole 47 so that the axle 38 cannot come off in the axial direction. The curved needle 2 may be configured as shown in FIG. 17: a fitting section 51 is arranged on the proximal side of the curved needle 2. A slit 52, perforation 49, and female sutured hole 50 are arranged on the arm section 45. The fitting section 51 is fit into the slit 52, and fixed with a bolt 48; and if the bolt 48 is removed, the curved needle 2 can be detached from the arm section 45 (forming a detachable structure).

The rotation disk 37, on which a bevel gear 40 is fixed as shown in FIG. 14, has a rotation axle 43, and is fit into the hole 53 arranged near the distal end of the endoscope 27. The C-ring 41 is arranged so that the rotation axle 43 cannot come out from the hole 53. As in the first embodiment, the operating wire 4 for rotating the rotation disk 37 is interlinked at least with part of the rotation disk 37 by brazing, soldering, or friction so that the power of the operating wire 4 can be positively transmitted without slippage.

Also as in the first embodiment on the proximal side, the two ends of the operating wire 4 are separately fixed to curved needle control sections 31 and 32. The curved needle 2 can be manipulated by alternately pushing and pulling the control sections 31 and 32. It is needless to say that the curved needle can be rotated forward and backward by manipulating the control sections 31 and 32. In such a way, the power transmission means 54 comprising the bevel gears 39 and 40 allows transmission of the power between the endoscope 27, and the suturing unit 36 comprising the curved needle 2 axle section 38, bevel gear 39, stop member 44, and protective member 46, while at the same time allowing the suturing unit 36 to be detachable. It is needless to say that the suturing unit 36 can remain fixed to the endoscope 27 if the detachable structure is unnecessary. In addition, although the power transmission means 54 is realized by bevel gears like 39 and 40, any other means which result in power transmission, while still allowing the suturing unit to be detachable from the endoscope 27 may be used. For example, a structure in which a motor is arranged on the side of unit 36, and electric contact between unit 36 and endoscope 27 is provided can be used.

Figure 15:
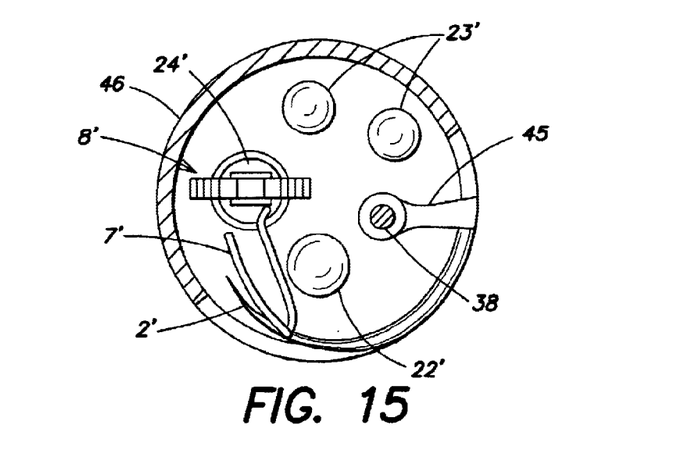
FIG. 15 is a sectional view taken along the line B—B of FIG. 14.
Figure 16:
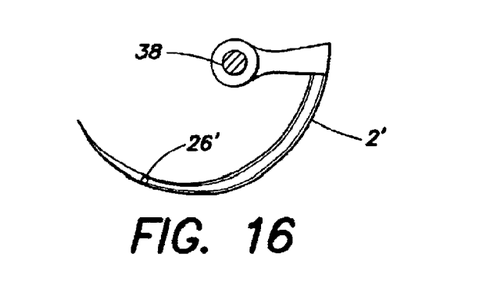
FIG. 16 is a detailed view of the curved needle 2.

On the other hand, as shown in FIG. 16, a small hole 26 through which a suture 7 can pass is arranged on the sharp-edged end side of the curved needle 2 and, as shown FIGS. 14 and 15, the suture 7 passes through the hole 26. As shown in FIG. 1 for the first embodiment, the proximal end portion of the suture 7 is removed from the body cavity from the channel opening 15 via the forceps channel 24.

As in the first embodiment, a suture grasping/withdrawing means 8 is detachably arranged inside the endoscopic suturing device 1 to grasp one end of the suture 7, and withdraw it from the body, after the curved needle 2 is stuck into a tissue. Although grasping forceps are used on the present embodiment as in the first embodiment, any appropriate tool may be used for the above-mentioned grasping and withdrawing operation. The suture grasping/withdrawing means 8 is situated at an appropriate location so as to grasp one end of the suture 7 in an easy manner. The suture 7 passes through the forceps channel 24 like the suture grasping/withdrawing means 8 A slider 33 is attached to the suture grasping control section 10: the grasping member 34 arranged on the distal end can be opened or closed to grasp the suture 7 by pushing or pulling the slider 33.

With reference to FIGS. 1, 14, and 15, the manner of assembling the second embodiment will be described. While the suturing unit 36 comprising a curved needle 2, axle 38, bevel gear 39, stop member 44, and protective member 46 remains detached from the endoscope 27, the suture 7 is pushed through the hole 26. The suture grasping/withdrawing means 8 is inserted from the channel opening 15, and, as shown in FIG. 1, one end of the suture 7 grasped by the suture grasping/withdrawing means 8 is taken out from the channel opening 15.

Next, the suturing unit 36 is fixed to the distal end of the endoscope 27 with a bolt 9". Next, the suture grasping/withdrawing means 8 is inserted into the forceps channel 24 like the suture 7 until in such a position that it can grasp the suture 7 after the needle is stuck into a tissue. The suture grasping/withdrawing means 8 may be inserted when the suture 7 is grasped and withdrawn after sticking.

The suturing process is the same as in the first embodiment.

Figure 19:
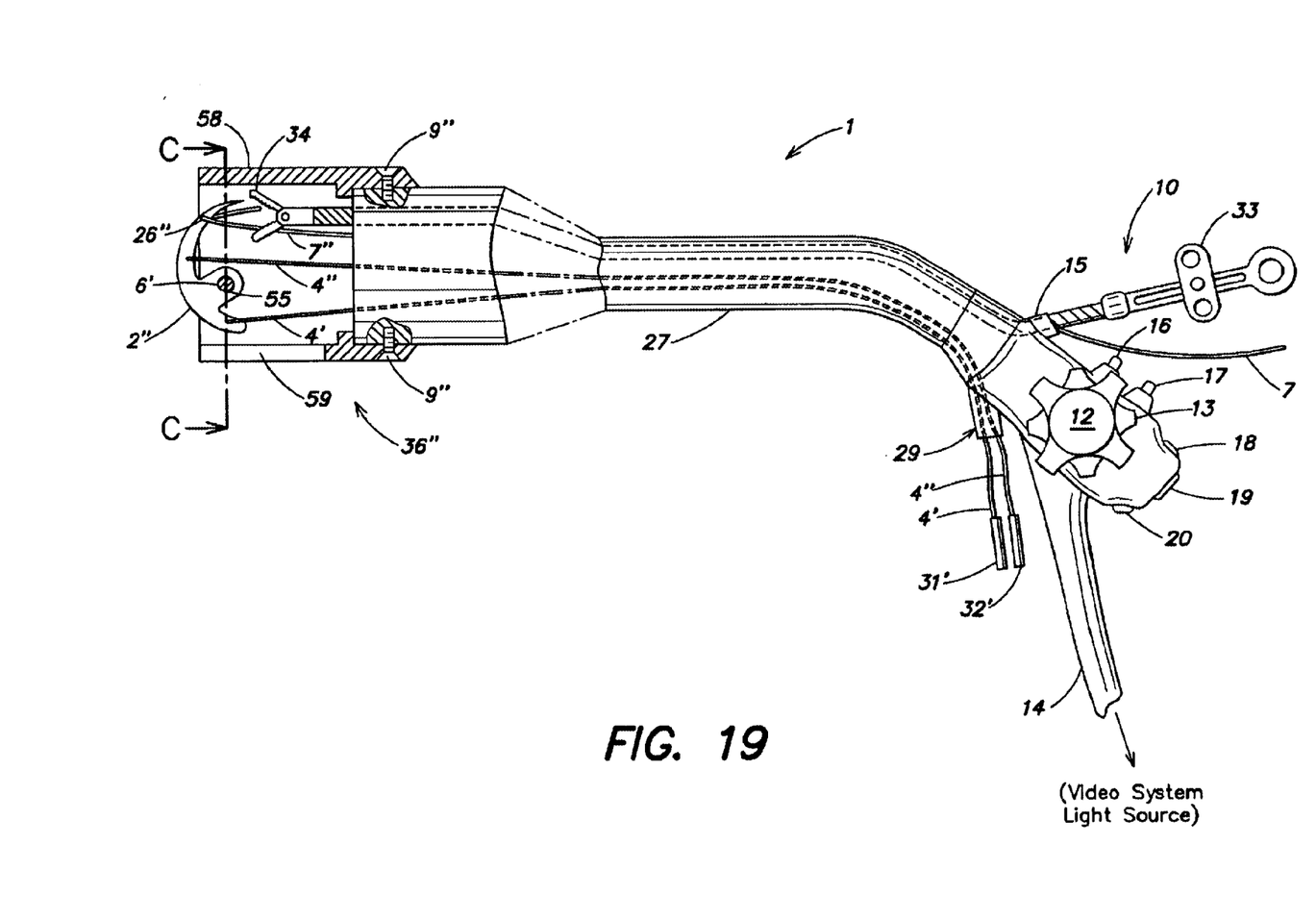
FIG. 19 is a view of the endoscopic suturing device 1 whose distal end portion is modified.
Figure 20:
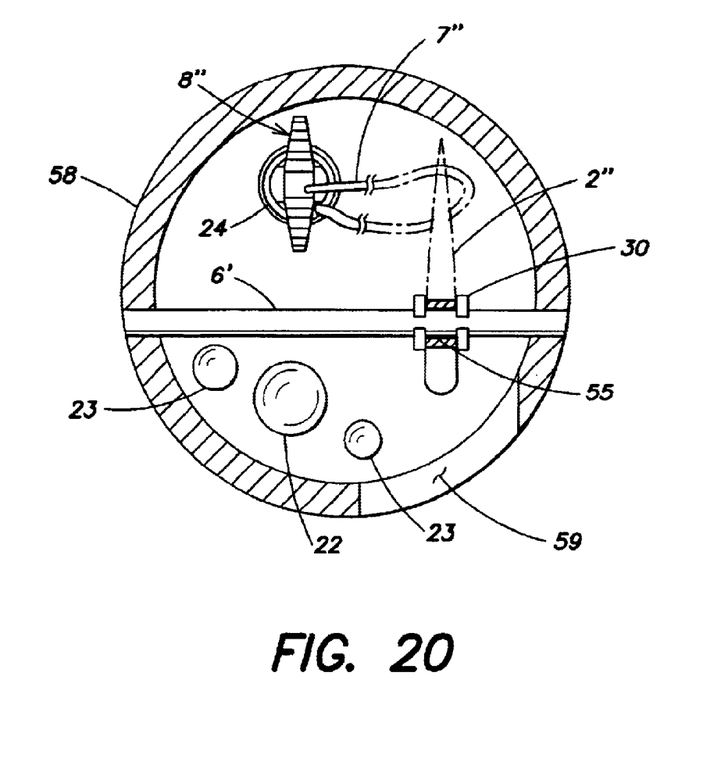
FIG. 20 is a sectional view taken along the line C—C of FIG. 19.
Figure 21:
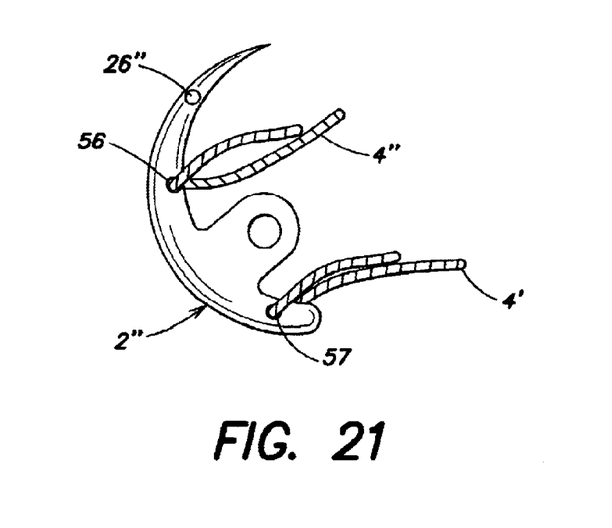
FIG. 21 is a different composition of the curved needle 2".

In addition to those merits listed for the first embodiment, several addition advantages are present in the second embodiment. Since the power transmission allows the suturing unit to be detached, the endoscope 27 and suturing unit 36 can be cleaned more appropriately; the suturing unit 36 can be a disposable component, or autoclaved; and the shape of protective member 46 or a slit 42 can be easily modified, A third embodiment of the present invention is shown in FIGS. 19–21. Again, since the proximal side of the endoscopic suturing device 1 has the same construction as that of the first embodiment, description is omitted. As in the first embodiment, a CCD camera 22, light guide 23, and forceps channel 24 are arranged in the distal end of the endoscope 27.

As shown in FIG. 19, a protective member 58 is detachably or integrally attached with a bolt 9" to the distal end of the endoscope 27 so that the curved needle 2" does not injure the human body when the endoscopic suturing device 1 is inserted into a body cavity, and a slit 59 is arranged so that the curved needle 2" can be rotated.

An axle 6' is fixed on the protective member 58 that is almost orthogonal to the longitudinal axle of the endoscope 27. The axle 6' is fit into the hole 55 of the curved needle 2", so that the curved needle 2" can be rotated. A stop member 30 like a C-ring is arranged so that the curved needle 2" cannot move on the axle 6' in the axial direction.

As shown in FIG. 19, the curved needle 2" is interlinked by operating wires 4' and 4" by brazing, soldering. Also, as shown in FIG. 21, the operating wires 4' and 4" are passed through the holes 56 and 57 of the curved needle by forming loops and fixed by blazing or soldering. On the proximal side, the two ends of the operating wires 4' an 4" are fixed to curved needle control sections 31 and 32 separately: the curved needle 2" can be manipulated by the control sections 31 and 32.

Other parts are the same as in the embodiment 1.

Assembling of the third embodiment is described in FIG. 19 and FIG. 20. While the suturing unit 36" comprising a curved needle 2", operating wires 4' and 4", a protective member 58 and an axle 6' is detached from the endoscope 27, the suture 7" is passed through the hole 26". The suture grasping/withdrawing means 8" is inserted from the channel opening 15, and as shown in FIG. 19, one end of the suture 7" grasped by the suture grasping/withdrawing means 8" is taken out from the channel opening 15.

Next, both ends of the operating wires 4' and 4" are grasped by the suture grasping/withdrawing means 8" and inserted from the curved needle driving mechanism fixation sections 29, and brought to the proximal side of the endoscope 27. Next, the suturing unit 36" is fixed to the distal end of the endoscope 27 with a bolt 9".

Then, the suture grasping/withdrawing means 8" is inserted into the forceps channel 24, like the suture 7", until such a position as can grasp the suture 7" after the needle is stuck into a tissue. The suture grasping/withdrawing means 8" may be inserted when the suture 7" is grasped and withdrawn after sticking.

The suturing process is the same as in the embodiment 1.

In addition to the merits listed for the first embodiment, in this third embodiment, the sticking force can be increased by the principle of leverage, due to the operating wires 4' and 4" fixed at a distance from the axle 6".

In all of the above embodiments, after the suture 7 is passed through the tissue, a knot is tied in the following manners:

For example, the distal end of the suture 7 is grasped by clamp forceps or the like and is withdrawn toward the proximal side through a channel provided within or along the periphery of the endoscope. Then the suture 7 is knotted, and the knot is moved by a pusher tube or the like toward the distal end of the endoscope through the channel to bind the tissue by the suture 7. Tying the knot may be repeated several times.

Instead of tying a knot, the suture 7 withdrawn toward the proximal side may be passed through a tube of rubber, and the tube of rubber is moved toward the distal end of the endoscope to bind the tissue. The tube of rubber may be replaced with a clip.

Further, clamp forceps may be inserted into the channel of the endoscope toward its distal end to tie a knot there to bind the tissue.

In each of the above manners, after the tissue has been bound, suture cutting forceps are inserted into the channel of the endoscope toward its distal end to cut a remaining part of the suture 7 while observing with the endoscope.

In summary, embodiments of the present invention have various advantages including:

(1.) The sticking force can be efficiently transmitted to the curved needle even though the endoscope is in any state of bending.

(2.) Since the suturing device is integrated with the endoscope, the general outer diameter can be reduced, and it can be inserted into a narrow body cavity.

(3.) Since the suturing device is integrated with the endoscope, it can be brought to the target region only by manipulating the endoscope.

(4.) Since the control section of suturing device is arranged near the control section of endoscope, the manipulability of the suturing device and the endoscope can be improved.

(5.) The curved needle can be inserted to the target region without injuring the body cavity.

(6.) The sticking location can be corrected.

(7.) The curved needle is detachable, and only the needle can be disposable.

(8.) Since the suturing unit is detachable, only the suturing unit can be disposable, and the endoscope can be cleaned more easily.

(9.) Since the suturing unit is detachable, only the suturing unit can be sterilized, for example, by autoclave.

(10.) Since the needle is curved, the depth of sticking can be changed by changing the curvature radius of needle.

(11.) Since the needle is curved, where the needle is stuck into a tissue, or removed from the tissue is confirmed through the field of view of endoscope.

(12.) In the case of first embodiment, suturing can be made in front of and tangent to the direction of the field of view of endoscope.

What is claimed is:

1. An endoscopic suturing device comprising:
   a flexible endoscope;
   a needle adapted to suture a tissue of a living body, said needle being one of: (i) detachably arranged at a distal end portion of said endoscope, and (ii) integrally embedded in said endoscope;
   a driving mechanism arranged on said endoscope to operate said needle,
   wherein said needle comprises at least one perforation through which a suture is passed from one side of the needle to the other side during a suturing operation.

2. An endoscopic suturing device comprising:
   a flexible endoscope;
   a needle adapted to suture a tissue of a living body, said needle being one of: (i) detachably arranged at a distal end portion of said endoscope, and (ii) integrally embedded in said endoscope;
   a driving mechanism arranged on said endoscope to rotate said needle, said driving mechanism including a flexible wire which is coupled to the needle; and
   a protective member arranged at a distal end portion of said endoscope to cover at least part of said needle so as to prevent undesired piercing of the tissue to be sutured.

3. An endoscopic suturing device according to claim 2, wherein the driving mechanism rotates the needle in a direction for piercing the tissue of the living body when one end of the flexible wire is pulled.

4. An endoscopic suturing device comprising;
   an endoscope,
   a needle detachably arranged at a distal end portion of or integrally embedded in said endoscope for suturing a tissue of a living body, the needle having an axle member as a rotation axis thereof which is coupled with the needle by an arm member;
   a suture for suturing said tissue with said needle;
   a driving mechanism arranged on said endoscope and operating said needle.

5. An endoscope suturing device of claim 4, wherein said driving mechanism comprises at least one wire.

6. An endoscopic suturing device of claim 4, wherein a grasping member adapted to grasp said suture is arranged on the distal end portion of said endoscopic suturing device.

7. An endoscopic suturing device of claim 4, wherein said needle has at least one perforation through which said suture is passable.

8. An endoscope suturing device comprising:

an endoscope;

a needle detachably arranged at a distal end portion of or integrally embedded in said endoscope for suturing a tissue of a living body, the needle having an axle member as a rotation axis thereof which is coupled with the needle by an arm member;

a suture for suturing said tissue with said needle;

a driving mechanism arranged on said endoscope and operating said needle; and at least one wire is wound or fixed on at least the cylindrical member.

9. An endoscopic suturing device of claim 8, wherein said needle has at least one perforation through which said suture is passable.

10. An endoscope suturing device comprising:

an endoscope;

a needle detachably arranged at a distal end portion of or integrally embedded in said endoscope for suturing a tissue of a living body, the needle having an axle member as a rotation axis thereof which is coupled with the needle by an arm member;

a suture for suturing said tissue with said needle; and a driving mechanism arranged on said endoscope and operating said needle, and wherein an axle member of said needle is fixed to a protective member covering at least part of said needle.

11. An endoscopic suturing device of claim 10, wherein a suturing unit comprising at least said needle, the rotation axis of said needle, and the protective member covering at least part of said needle is detachably arranged on the distal end portion of said endoscope.

12. An endoscopic suturing device of claim 10, wherein said needle has at least one perforation through which said suture is passable.

13. An endoscopic suturing device comprising:

a flexible endoscope;

a needle rotatably arranged relative to the endoscope;

a first flexible wire arranged along the endoscope and connected to the needle to rotate the needle in a direction for piercing a living body tissue when the first flexible wire is pulled; and a second wire arranged along the endoscope and connected to the needle to rotate the needle in a direction for removing the needle out of the living body tissue when the second flexible wire is pulled.

14. An endoscopic suturing device comprising:

a flexible endoscope having an observation window at a distal end portion;

a needle adapted to suture a tissue of a living body, said needle being one of: (i) detachably arranged at a distal end portion of said endoscope, and (ii) integrally embedded in said endoscope;

a driving mechanism arranged on the endoscope to operate the needle; and a protective member comprising a cylindrical member attached at the distal end portion of the flexible endoscope for covering at least a part of the needle so as to prevent undesired piercing of the tissue to be sutured, wherein a top end of the protective member is positioned on a distal side of the observation window.

* * * * *

UNITED STATES PATENT AND TRADEMARK OFFICE
CERTIFICATE OF CORRECTION

PATENT NO. : 6,719,763 B2
DATED : April 13, 2004
INVENTOR(S) : Sydney Chung

Page 1 of 1

It is certified that error appears in the above-identified patent and that said Letters Patent is hereby corrected as shown below:

Title page,
Item [75], Inventors, add -- ; Chika Shiro, Hachioji (JP) --.

Signed and Sealed this

Twenty-eighth Day of February, 2006

JON W. DUDAS
*Director of the United States Patent and Trademark Office*